United States Patent [19]

Jensen

[11] Patent Number: 5,042,289
[45] Date of Patent: Aug. 27, 1991

[54] CONTAINER END TEST SYSTEM

[75] Inventor: Eric L. Jensen, Chesterfield County, Va.

[73] Assignee: Reynolds Metals Company, Richmond

[21] Appl. No.: 568,795

[22] Filed: Aug. 17, 1990

[51] Int. Cl.5 .............................................. G01M 3/26
[52] U.S. Cl. ...................................................... 73/40
[58] Field of Search ...................... 73/37, 40, 49.8, 45.2

[56] References Cited

U.S. PATENT DOCUMENTS 3,792,606  2/1974  Munger ................................... 73/40
3,954,003  5/1976  Dobbins .................................. 73/40
4,194,388  3/1980  Mack ...................................... 73/37
4,440,016  4/1984  Konagaya et al. ..................... 73/40

Primary Examiner—Hezron E. Williams
Attorney, Agent, or Firm—Alan T. McDonald

[57] ABSTRACT

End closure for a container is tested for pneumatic pressure required to buckle or rupture it, by applying pneumatic test pressure to one face of the closure, and using that pressure to press an annular peripheral area of the opposite face of the closure against a support to establish a seal without gripping the closure mechanically.

4 Claims, 2 Drawing Sheets

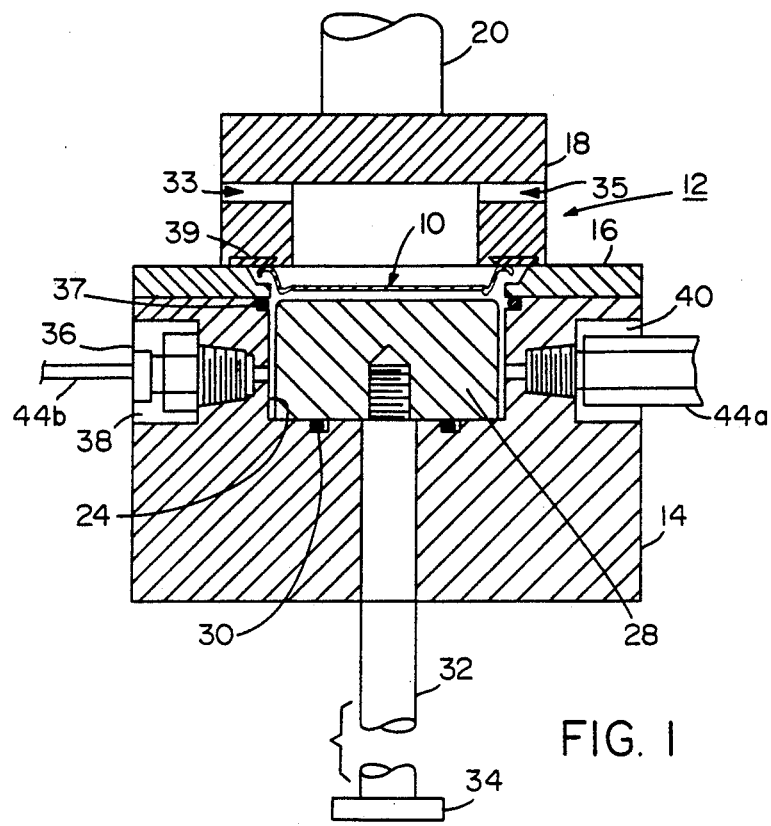
FIG. 1
FIG. 2
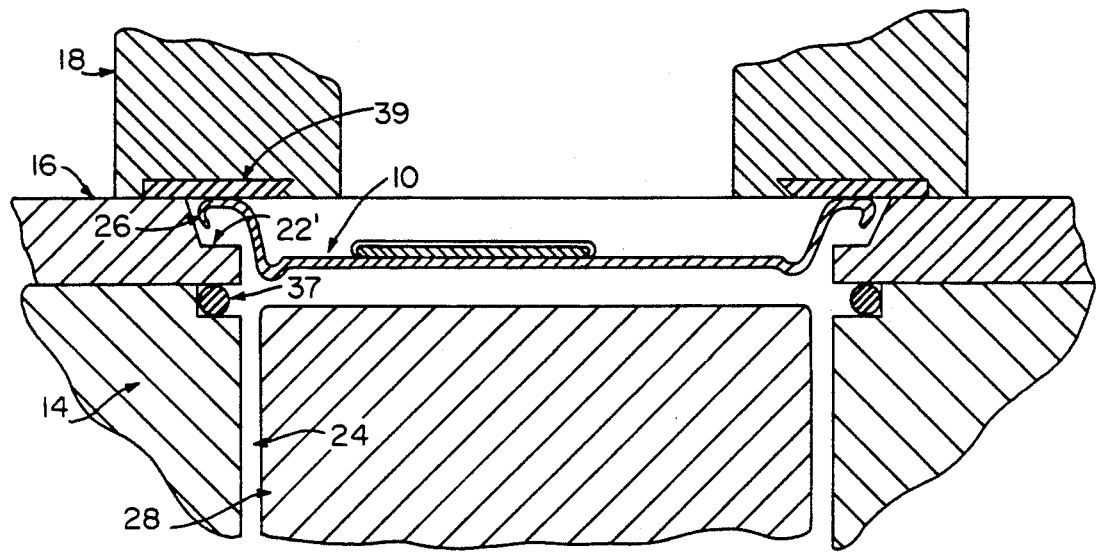

CONTAINER END TEST SYSTEM

BACKGROUND OF THE INVENTION

Easy-open can ends of aluminum base alloys have been perfected and marketed over the years with the constant objective of obtaining high quality at minimum cost. Testing of ends to maintain their quality is essential.

The ideal test is to seam an end on a can body and inject air under pressure into the can until the end fails, either through rupture along the scoring necessary for easy opening, or by buckling of unscored portions of the end. This has become the conventional test, in spite of the trouble and expense of performing it. Unfortunately, testing an end by itself has involved mechanical clamping to hold it in place and in sealed relation to the test equipment, and the test results in that case do not correlate reliably with results of testing while seamed on a can body. The result is that testing is not regularly done at the end of each production line and this has inhibited further progress in reducing the amount of metal in ends, which is a significant factor in their cost.

SUMMARY OF THE INVENTION

In accordance with the present invention, a can or other container end is pressed against a seal during testing only by the pneumatic pressure used to test the end. The distortion of mechanical clamping is thereby avoided, and the test results correlate well with those obtainable by seaming the end on a can body and applying pressure within the can until failure of the end.

The testing method and apparatus of the invention makes it possible to make quick tests of many ends selected intermittently from an end production line, and to display the results where the operator of the line can see them, or to sound an alarm when an end fails at a lower than acceptable pressure level. The operator of a can end production line is thus alerted to act promptly when test results indicate trouble in the line.

Other objects, advantages and details of the invention will become apparent as the following disclosure proceeds.

DRAWINGS ILLUSTRATING THE INVENTION

The present preferred embodiment of the invention is shown in the following drawings, in which:

FIG. 1 shows semi-schematically a view of a section through the central axis of can end testing apparatus in accordance with the invention;

FIG. 2 shows an enlarged detailed view of a portion of the apparatus shown in FIG. 1;

DETAILED DESCRIPTION OF PRESENT PREFERRED EMBODIMENT

Figure 3:
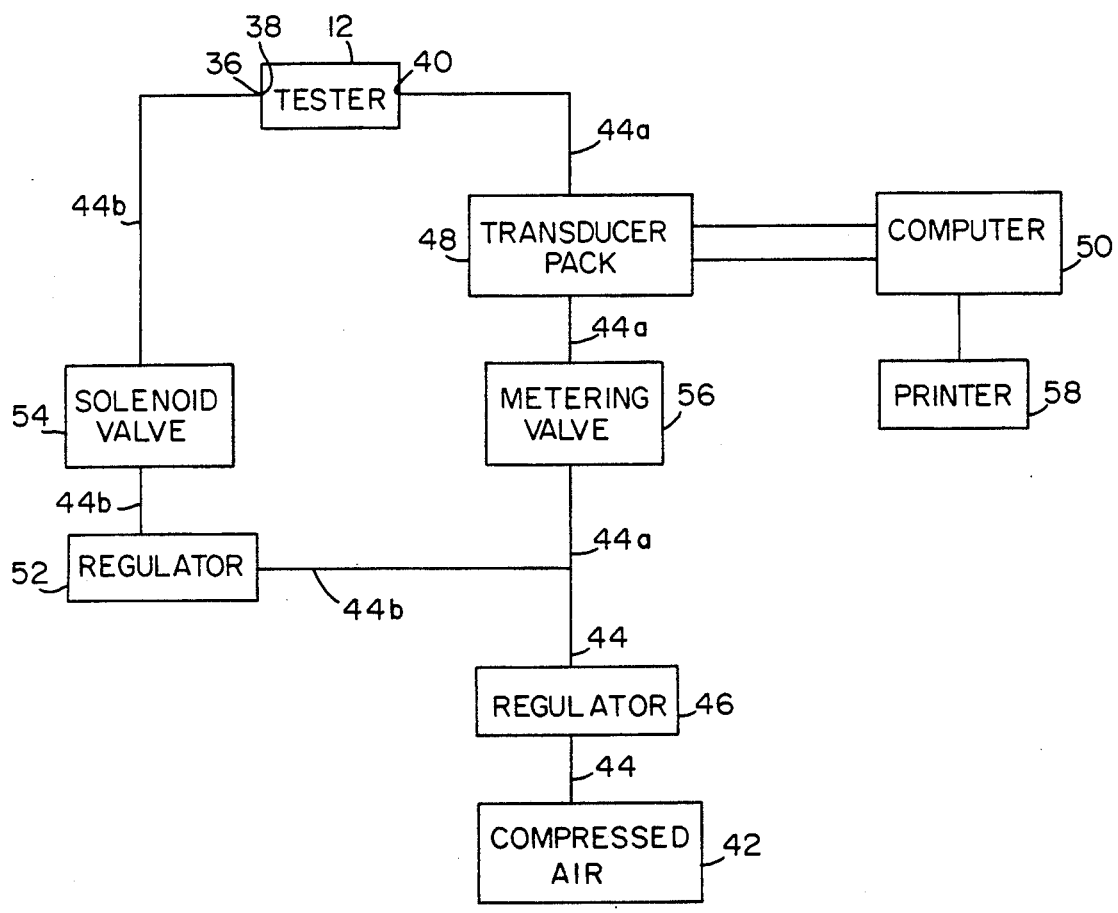
FIG. 3 shows schematically the testing apparatus shown in FIG. 1 and auxiliary apparatus for operating within the testing apparatus.

Referring now more particularly to the drawings, and initially to FIG. 1, an easy open can end 10 is shown where initially placed in a can end tester 12 of the invention.

The tester 12 has a cylindrical main body block 14, a cylindrical cover plate 16 secured to block 14, a cylindrical removable cap 18, and means 20 operable to press cap 18 down against plate 16 with considerable force (e.g. about 1,000 pounds) and to lift cap 18 away from plate 16. A circular opening 22 through plate 16 is aligned with and opens into a cylindrical opening 24 into the block 14. Plate 16 is relieved around the upper end of opening 22 to provide a recess 22' on which the flange 26 around end 10 can rest before air pressure is applied.

A cylindrical ejector head 28 is enclosed within the block cavity 24. When head 28 is retracted, its bottom surface rests on block 14 at the bottom of cavity 24 and is sealed thereto by O-ring 30 in a circular groove in block 14. Head 28 has a diameter enough less than the diameter of block cavity 24 to permit passage of compressed air between head 28 and block 14 during testing of end 10. The top of head 28 is spaced beneath end 10 when its flange 26 is resting on recess 22' and head 28 is in retracted position.

A stem 32 extends slidably through block 14 to attach to the bottom of ejector head 28. An activating means 34, such as a solenoid or pneumatic cylinder, operates stem 32 to raise head 28 after testing of an end is completed and cap 18 has been lifted. Head 28 then lifts the tested end above plate 16, where it may be removed by any suitable means, such as a lateral pushing means. Head 28 is then returned to its lowermost position, ready for the next testing cycle.

A pair of side openings 33 and 35 extend through cap 18 to permit air pressure within cap 18 above test end 10 to equalize with atmospheric pressure outside of the cap. A pair of side openings 38 and 40 extend through block 14 to supply compressed air to cavity 24 beneath test end 10. When testing of an end 10 is to begin, compressed air is first supplied through opening 38 through a check valve 36 which permits flow of air through opening 38 into cavity 24 but opposes reverse flow. An O-ring 37 seals the inner face between block 14 and plate 16 so that the air enters the space between end 10 and ejector head 28 and lifts end 10 until the top of its peripheral flange 26 presses against a washer-like circular elastomeric sealing member 39 mounted on the bottom of cap 18. The outer margin of seal 39 extends between the top of plate 16 and the bottom of cap 18, and its inner margin is supported by the bottom of cap 18 against pressure from flange 26 of end 10 during pressure testing. Compressed air at progressively higher pressures is then supplied through opening 40. The more the air pressure increases against the lower surface of end 10 the harder flange 26 presses against seal 39 to prevent escape of air therebetween, until end 10 finally buckles or ruptures.

The tester 12 is connected to a system for supplying compressed air at increasing pressures until a lid in the tester buckles, and for recording the pressure when the buckle occurs, as will now be described.

As shown in FIG. 3, source of compressed air 42 is connected to a line 44 having one branch 44a leading to opening 40, and another branch 44b leading to opening 38 through check valve 36. A regulator 46 limits air pressure (e.g., to 120 psi) supplied to both branches. A transducer pack 48 registers pressure in branch 44a and signals a computer 50 accordingly.

A regulator 52 in branch 44b limits the pressure of air supplied to inlet 38 (e.g., to 25-30 psi). When a testing cycle begins, computer 50 opens a solenoid valve 54 in branch 44b, and the resulting inflow of air through opening 38 lifts end 10 to cause it to press against the sealing member 39, as previously described. Computer 50 then activates a metering valve 56 in branch 44a, to start incremental increases of air pressure in branch 44a, timed so that computer 50 can register the increases in small increments of a pound or so of air pressure and cause them to print out progressively on a printer 58. Such increases continue until pressure is built up to the point where end 10 finally buckles or ruptures. This causes enough drop in pressure in branch 44a to cause computer 50 to close valves 54 and 56, and to activate means 34 to raise head 28, as previously described.

While present preferred embodiments and methods of practicing the invention have been illustrated and described, it will be understood that the invention is not limited thereto, but may be otherwise variously embodied and practiced within the scope of the following claims.

I claim:

1. A container end tester, comprising a pair of separable elements adapted to enclose a container end without clamping against opposite portions of the container end, circular sealing means mounted on one of said elements and adapted to seal against an outer circular margin of the container end when one face of the container end is pressed toward said one element, and means to increase pneumatic pressure against the other face of the container end relative to pneumatic pressure against said one face of the container end, thereby pneumatically pressing the container end against said sealing means with force supplied substantially entirely by the difference between the pneumatic pressures on opposite faces of the container end.

2. A container end tester in accordance with claim 1, comprising means to supply compressed air to a space between said other face and one of said elements, means sealing said space against escape of compressed air, and means connecting to atmospheric pressure a space between said one face and the other of said elements.

3. A container end tester in accordance with claim 1, comprising means to support the container end out of contact with said sealing means before air pressure is applied, the container end being movable into contact with said sealing means only by said compressed air.

4. A method of testing a container end, comprising applying a greater pneumatic pressure against one face of the container end than against the opposite face, thereby generating a force against said one face, said force moving the container end into contact with a fixed circular sealing means, applying substantially only said force to press an outer circular margin of said opposite face of the container end against said sealing means, and increasing the difference in pressure until failure of the container end through buckling or rupture.

* * * * *